(12) United States Patent
Shudo et al.

(10) Patent No.: US 8,198,329 B2
(45) Date of Patent: Jun. 12, 2012

(54) MEMORY CONSOLIDATION PROMOTING AGENT AND METHOD OF USE

(75) Inventors: Koichi Shudo, Tokyo (JP); Hiroyuki Kagechika, Tokyo (JP)

(73) Assignees: Research Foundation Itsuu Laboratory, Tokyo (JP); Kemphys Ltd., Tokyo (JP)

( * ) Notice: Subject to any disclaimer, the term of this patent is extended or adjusted under 35 U.S.C. 154(b) by 1155 days.

(21) Appl. No.: 10/598,709

(22) PCT Filed: Mar. 9, 2005

(86) PCT No.: PCT/JP2005/004051
§ 371 (c)(1),
(2), (4) Date: Jun. 8, 2007

(87) PCT Pub. No.: WO2005/087219
PCT Pub. Date: Sep. 22, 2005

(65) Prior Publication Data
US 2008/0021108 A1      Jan. 24, 2008

Related U.S. Application Data

(60) Provisional application No. 60/622,618, filed on Oct. 28, 2004.

(30) Foreign Application Priority Data

Mar. 10, 2004  (JP) .................................. 2004-066996

(51) Int. Cl.
*A01N 37/10* (2006.01)
*A01N 31/04* (2006.01)
*A61K 31/19* (2006.01)
*A61K 31/07* (2006.01)

(52) U.S. Cl. ........................................ 514/568; 514/725
(58) Field of Classification Search .................. 514/568, 514/725
See application file for complete search history.

(56) References Cited

U.S. PATENT DOCUMENTS

| | | | |
|---|---|---|---|
| 5,965,606 A | 10/1999 | Teng et al. | |
| 6,093,838 A | 7/2000 | Vasudevan et al. | |
| 6,127,382 A | 10/2000 | Beard et al. | |
| 6,534,544 B1 | 3/2003 | Teng et al. | |
| 2003/0008919 A1 | 1/2003 | Roullet | |
| 2004/0082550 A1 | 4/2004 | Kagechika | |
| 2008/0139842 A1 | 6/2008 | Shudo et al. | |
| 2008/0182905 A1 | 7/2008 | Takenaga et al. | |
| 2008/0207768 A1 | 8/2008 | Shudo et al. | |
| 2008/0214668 A1 | 9/2008 | Roullet | |
| 2008/0255069 A1 | 10/2008 | Shudo et al. | |

FOREIGN PATENT DOCUMENTS

| | | | |
|---|---|---|---|
| EP | 0 906 907 A1 | 4/1999 | |
| EP | 1 277 729 A1 | 1/2003 | |
| EP | 1357104 A1 | 10/2003 | |
| EP | 1500401 A1 | 1/2005 | |
| JP | 10-059951 | 3/1998 | |
| JP | 10-338658 | 12/1998 | |
| JP | 2000-502707 | 3/2000 | |
| JP | 2002-332266 | 11/2002 | |
| WO | 97/24116 A2 | 7/1997 | |
| WO | 97/24116 A3 | 7/1997 | |
| WO | 98/45242 A1 | 10/1998 | |
| WO | 02/26727 A2 | 4/2002 | |
| WO | 02/28810 A2 | 4/2002 | |

OTHER PUBLICATIONS

Samad et al. "Regulation of dopaminergic pathways by retinoids: Activation of the D2 receptor promoter by members of the retinoic acid receptor-retinoid X receptor family" *Proc. Natl. Acad. Sci. USA* 94:14349-14354, 1997.

Etchamendy et al. "Alleviation of a Selective Age-Related Relational Memory Deficit in Mice by Pharmacologically Induced Normalization of Brain Retinoid Signaling" *J. Neurosci.* 21(16):6423-6429, 2001.

de Thé et al. "Retinoids: 10 Years On. The Retinoic Acid Receptors" Basel, Karger, pp. 2-9, 1991.

Goodman et al. "Evidence for defective retinoid transport and function in late onset Alzheimer's disease" *Proc. Natl. Acad. Sci. USA* 100(5):2901-2905, 2003.

Bourdel-Marchasson et al. "Antioxidant defences and oxidative stress markers in erythrocytes and plasma from normally nourished elderly Alzheimer patients" *Age and Ageing* 30:235-241, 2001.

Yamakawa et al. "Retinobenzoic Acids. 5. Retinoidal Activities of Compounds Having a Trimethylsilyl or Trimehylgermyl Group(s) in Human Promyelocytic Leukemia Cells HL-60" *J. Med. Chem.* 33:1430-1437, 1990.

Hiraga, Y. "Effects of scopolamine upon delayed radial-arm maze performance in rats" *Folia pharmacol. japon.* 97:351-359, 1991.

Hashimoto, Y. "Retinobenzoic Acids and Nuclear Retinoic Acid Receptors" *Cell Structure and Function* 16:113-123, 1991.

Hashimoto et al. "Expression of Retinoic Acid Receptor Genes and the Ligand-Binding Selectivity of Retinoic Acid Receptors (RAR's)" *Biochem. Biophys. Res. Commun.* 166(3):1300-1307, 1990.

Database WPI Week 199849, Thomson Scientific, London, GB; AN 1998-583173.

Cocco et al.; "Vitamin A deficiency produces spatial learning and memory impairment in rats." Neuroscience, vol. 115, No. 2, 2002, pp. 475-482.

(Continued)

*Primary Examiner* — Sreeni Padmanabhan
*Assistant Examiner* — Uma Ramachandran
(74) *Attorney, Agent, or Firm* — Greenblum & Bernstein, PLC

(57) ABSTRACT

A medicament for promoting memory consolidation, which comprises, as an active ingredient, a non-natural retinoid, preferably a retinoid having a basic skeleton comprising an aromatic ring bound with an aromatic carboxylic acid or tropolone by means of a bridging group, more preferably 4-[(5,6,7,8-tetrahydro-5,5,8,8-tetramethyl-2-naphthalenyl) carbamoyl]benzoic acid or 4-[(3,5-bis-trimethylsilylphenyl)-carboxamido]benzoic acid.

7 Claims, No Drawings

OTHER PUBLICATIONS

Etchamendy et al., Database Biosis [Online), Biosciences Information Service, Philadelphia, PA, US; 2000, "Evidence for a role of vitamin A in higher cognitive functions"; Database accession No. PREV200100120509, which is a family member of Society for Neuroscience Abstracts, vol. 26, No. 1-2, 2000, pp. Abstract No.-652. 9, 30th Annual Meeting of the Neuroscience; New Orleans, Nov. 4-9, 2000.

O Donnell et al., Database Biosis [Online] Biosciences Information Service, Philadelphia, PA, US; 2003, "Retinoic acid displays promnesic activity in avoidance conditioning and spatial learning paradigms"; Database accession No. PREV200400205133; which is a family member of Society for Neuroscience Abstract Viewer and Itinerary Planner, vol. 2003, 2003, pp. Abstract No. 836.11 URL-http://sf, 33rd Annual Meeting of the Society of Neuroscience; New Orleans, LA, USA; Nov. 8-12, 2003.

Yoshimura et al., "Discovery of novel and potent retinoic acid receptor alpha agonists: syntheses and evaluation of benzofuranyl-pyrrole and benzothiophenyl-pyrrole derivatives."; Journal of Medicinal Chemistry, vol. 43, No. 15, Jul. 27, 2000; pp. 2929-2937.

Shudo et al.; "A synthetic retinoid Am80 (tamibarotene) rescues the memory deficit caused by scopolamine in a passive avoidance paradigm." Biological & Pharmaceutical Bulletin, vol. 27, No. 11, Nov. 2004, pp. 1887-1889.

Supplemental European Search Report issued in connection with EP 05720323 on Jun. 14, 2010.

MEMORY CONSOLIDATION PROMOTING AGENT AND METHOD OF USE

CROSS-REFERENCE TO RELATED APPLICATIONS

The present application is a national stage of International Application No. PCT/JP2005/004051, filed Mar. 9, 2005, which claims the benefit of Provisional Application No. 60/622,618, filed Oct. 28, 2004, and also claims priority to Japanese Patent Application No. 2004-066996, filed Mar. 10, 2004.

TECHNICAL FIELD

The present invention relates to a medicament which promotes memory consolidation.

BACKGROUND ART

Memory is a system in which nerves make complicated neural circuits in the brain with growth thereof, and specific information is consolidated in the neural circuits in a reproducible state. It was discovered that destroyed connecting synapses of nerves were restored in the hippocampus of the limbic system which is responsible for memory. It came to be inferred that new neural circuits are formed in the brain depending on the necessity for memory. It has also become revealed that hierarchical levels of memory exist, such as preservation of short-term memory and long-term memory and reproduction thereof. Short-term memory corresponds to a level that information is preserved only a short time, and then when it becomes necessary to memorize that information, the short-term memory changes to long-term memory, and this information is consolidated as memory which is not easily forgotten. It is considered that long-term memory is transmitted from the hippocampus to the cerebral cortex and stored in the cerebral cortex over many hours. Long-term memory is classified into declarative memory and procedural memory depending on a content to be memorized. Declarative memory is memory which can be explained by means of language, and procedural memory is what is called as memory of skill, which is acquired by a person and unconsciously used by the person. Declarative memory may sometimes be further classified into episodic memory and semantic memory. Episodic memory is memory of personal experience and semantic memory is that of general knowledge and information such as those acquired by study. The episodic memory is mainly obstructed in the Alzheimer disease, and in the disease, patients often cannot memorize experiences, i.e., what, when and where they have done.

Retinoid is a generic term for referring to compounds that bind to receptors required for all trans-retinoic acid and 9-cis-retinoic acid to exhibit physiological functions thereof (three kinds of subtypes of the receptor exist for each compound), and thereby exhibit actions similar to those of retinoic acid or a part of the actions. Concerning the action of retinoid on neurodegenerative diseases, for example, it has been suggested that the retinoids described in Japanese Patent Unexamined Publication (KOHYO) No. 2000-502707 are effective for neurodegenerative diseases (e.g., Alzheimer disease). It has also been reported that expression of dopamine D2 receptor is increased by activation of a retinoid receptor (Proc. Natl. Acad. Sci., USA, 94, pp. 14349-14354, 1997). As for relationship between a retinoid and memory, it has been reported that reduction of memory in aged mice is recovered by retinoic acid (150 µg/kg, s.c.) (J. Neurosci., 21, pp. 6423-6429, 2001). However, what is suggested in this article is suppression of reduction of already consolidated long-term memory by retinoic acid, and the article does not suggest nor teach any action of retinoic acid on the consolidation process of short-term memory to long-term memory.

[Patent document 1] Japanese Patent Unexamined Publication (KOHYO) No. 2000-502707
[Non-patent document 1] J. Neurosci., 21, pp. 6423-6429, 2001

DESCRIPTION OF THE INVENTION

Object to be Achieved by the Invention

An object of the present invention is to provide a medicament for preventing and treating dysfunction of memory consolidation associated with neurodegenerative diseases and the like. More specifically, the object of the present invention is to provide a medicament for prophylactic and/or therapeutic treatment of hypomnesia associated with neurodegenerative diseases and the like by promoting memory consolidation.

The inventors of the present invention conducted various researches to achieve the aforementioned object, and as a result, they found that a retinoid, having a basic skeleton comprising an aromatic ring bound with an aromatic carboxylic acid or tropolone by means of a bridging group, had a superior memory consolidation promotion effect, and this retinoid successfully exhibited remarkably high efficacy for prophylactic and/or therapeutic treatment of dysfunction of memory consolidation associated with neurodegenerative diseases such as Alzheimer disease and the like. The present invention was achieved on the basis of the above findings.

The present invention thus provides a medicament for promoting memory consolidation, which comprises as an active ingredient a non-natural retinoid, preferably a retinoid having a basic skeleton comprising an aromatic ring bound with an aromatic carboxylic acid or tropolone by means of a bridging group. This medicament can be used, for example, as a medicament for prophylactic and/or therapeutic treatment of dysfunction of memory consolidation associated with neurodegenerative diseases such as Alzheimer disease.

According to preferred embodiments of the present invention, there are provided the aforementioned medicament, wherein the retinoid is a retinoid that binds to the retinoic acid receptor (RAR) subtype α and subtype β, and does not substantially bind to the retinoic acid receptor subtype γ; the aforementioned medicament, wherein the retinoid is a retinoid having a basic skeleton comprising a substituted phenyl group and benzoic acid or tropolone bound through a bridging group; the aforementioned medicament, wherein the retinoid is 4-[(5,6,7,8-tetrahydro-5,5,8,8-tetramethyl-2-naphthalenyl)carbamoyl]benzoic acid or 4-[(3,5-bis-trimethylsilylphenyl)carboxamido]benzoic acid; the aforementioned medicament, wherein the retinoid is a retinoid comprising dibenzo[b,f][1,4]thiazepinylbenzoic acid as a basic skeleton; the aforementioned medicament, wherein the retinoid is 4-[2,3-(2,5-dimethyl-2,5-hexano)dibenzo[b,f][1,4]-thiazepin-11-yl]benzoic acid; and the aforementioned medicament, wherein the retinoid is 4-[5-(4,7-dimethylbenzofuran-2-yl)pyrrol-2-yl]benzoic acid.

From another aspect, the present invention provides use of the aforementioned retinoid for manufacture of the aforementioned medicament; and a method for promoting memory consolidation, which comprises the step of administrating an effective amount of the aforementioned retinoid to a mammal including human.

From a still further aspect, the present invention provides a medicament for prophylactic and/or therapeutic treatment of a neurodegenerative disease, preferably Alzheimer disease or Parkinson's disease, which comprises 4-[(5,6,7,8-tetrahydro-5,5,8,8-tetramethyl-2-naphthalenyl)carbamoyl]benzoic acid or 4-[(3,5-bis-trimethylsilylphenyl)carboxamido]benzoic acid as an active ingredient.

Effect of the Invention

The medicament of the present invention has a superior action for memory consolidation, and the medicament is useful as, for example, a medicament for prophylactic and/or therapeutic treatment of dysfunction of memory consolidation associated with neurodegenerative diseases such as Alzheimer disease.

BEST MODE FOR CARRYING OUT THE INVENTION

As the active ingredient of the medicament of the present invention, non-natural retinoids, preferably retinoids having a basic skeleton comprising an aromatic ring bound with an aromatic carboxylic acid or tropolone by means of a bridging group can be used. More specifically, as the active ingredient of the medicament of the present invention, retinoids represented by the following general formula: B—X-A (wherein B represents an aromatic group which may have a substituent, X represents a bridging group, and A represents a carboxylic acid-substituted aromatic group or tropolonyl group) can be used. In the specification, retinoid refers to compounds that bind to receptors required for all trans-retinoic acid and 9-cis-retinoic acid to exhibit physiological functions thereof, and thereby exhibit actions similar to those of retinoic acid or a part of the actions, and the term means compounds that have at least one retinoid-like action, for example, one ore more of cell differentiating action, cell proliferation promoting action, life supporting action, and the like. Whether a certain compound is a retinoid or not can be readily determined by the method described in H. de The, A. Dejean, "Retinoids: 10 years on.", Basel, Karger, 1991, pp. 2-9. Further, while retinoids generally have a property of binding to a retinoic acid receptor (RAR), the retinoid used as the active ingredient of the medicament of the present invention is preferably a retinoid that binds to the subtype α (RAR α) and subtype β (RAR β) of RAR, and does not substantially bind to the subtype γ (RAR γ). Binding to a retinoic acid receptor subtype can also be easily confirmed by the method described in the aforementioned literature.

As the aromatic group represented by B, a phenyl group which may have a substituent is preferred. Type, number, and substituting position of the substituent on the phenyl group are not particularly limited. As the substituent on the phenyl group, for example, a lower alkyl group can be used (in the specification, the term "lower" means a carbon number of 1 to about 6, preferably 1 to 4). As the lower alkyl group, an alkyl group having a linear or branched chain is preferred, and more specific examples include methyl group, ethyl group, n-propyl group, isopropyl group, n-butyl group, sec-butyl group, tert-butyl group, and the like. Other examples of the substituent on the phenyl group include, for example, a lower alkoxyl group such as methoxy group, a halogen atom (the halogen atom may be any of fluorine atom, chlorine atom, bromine atom, and iodine atom), a lower alkyl-substituted silyl group such as trimethylsilyl group, and the like. As the phenyl group, for example, a phenyl group substituted with 2 to 4 of lower alkyl groups, a phenyl group substituted with 1 or 2 of tri(lower alkyl)silyl group, And the like are preferred, and a phenyl group substituted with 2 to 4 of lower alkyl groups, a phenyl group substituted with 2 of tri(lower alkyl)silyl groups, and the like are more preferred.

When two of the lower alkyl groups substituting on the phenyl group are adjacent to each other, they may combine together to form one or two, preferably one of 5- or 6-membered ring together with the ring-constituting carbon atoms of the phenyl group to which they bind. The ring formed as described above may be saturated or unsaturated, and one or more lower alkyl groups such as methyl group and ethyl group may substitute on the ring. On the aforementioned formed ring, preferably 2 to 4 of methyl groups, more preferably 4 of methyl groups, may substitute. For example, it is preferred that two adjacent lower alkyl groups which substitute on the phenyl ring combine together to form 5,6,7,8-tetrahydronaphthalene ring, 5,5,8,8-tetramethyl-5,6,7,8-tetrahydronaphthalene ring, or the like. As the aromatic group represented by B, an aromatic heterocyclic group may also be used. Examples of such retinoid include a retinoid wherein B is a benzofuranyl group which may have a substituent, preferably benzofuran-2-yl group, particularly preferably 4,7-dimethylbenzofuran-2-yl group.

As the carboxylic acid-substituted aromatic group represented by A, a carboxylic acid-substituted phenyl group, a carboxylic acid-substituted heterocyclic group, and the like can be used, and 4-carboxyphenyl group is preferred. Examples of the heterocyclic carboxylic acid constituting the carboxylic acid-substituted heterocyclic group represented by A include, for example, pyrimidine-5-carboxylic acid, and the like. As the tropolonyl group represented by A, tropolon-5-yl group is preferred.

Type of the bridging group represented by X is not particularly limited, and examples include, for example, —NHCO—, —CONH—, —N($R^A$)— ($R^A$ represents a lower alkyl group, for example, cyclopropylmethyl group and the like), —C($R^B$)($R^C$)— ($R^B$ and $R^C$ independently represent hydrogen atom, a lower alkyl group, and the like). Further, X may be a divalent aromatic group. For example, X may be pyrrol-diyl group, or the like. Furthermore, the bridging group represented by X and the aromatic group represented by B may combine together to form a ring structure. For example, the basic skeleton of the retinoid represented by B—X-A may be dibenzo[b,f][1,4]thiazepinylbenzoic acid or dibenzo[b,f][1,4]diazepinylbenzoic acid. In the specification, the term "basic skeleton" means a main chemical structure for one or more arbitrary substituents to bind thereto.

As preferred retinoids, for example, retinoids comprising a phenyl-substituted carbamoylbenzoic acid or a phenyl-substituted carboxamidobenzoic acid as a basic skeleton can be used. Various retinoids comprising a phenyl-substituted carbamoylbenzoic acid or a phenyl-substituted carboxamidobenzoic acid as a basic skeleton are known. Typical examples of retinoids having a phenyl-substituted carbamoylbenzoic acid as a basic skeleton include Am80 (4-[(5,6,7,8-tetrahydro-5,5,8,8-tetramethyl-2-naphthalenyl)carbamoyl]benzoic acid (refer to Hashimoto, Y., Cell Struct. Funct., 16, pp. 113-123, 1991; Hashimoto, Y, et al., Biochem. Biophys. Res. Commun., 166, pp. 1300-1307, 1990), and typical examples of retinoids having a phenyl-substituted carboxamidobenzoic acid include Tac101 (4-[(3,5-bis-trimethylsilylphenyl)carboxamido]benzoic acid (J. Med. Chem., 33, pp. 1430-1437, 1990).

Preferred retinoids include, for example, compounds represented by the following general formula (I):

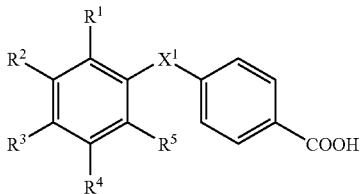

[Formula 1]

wherein $R^1$, $R^2$, $R^3$, $R^4$, and $R^5$ independently represent hydrogen atom, a lower alkyl group, or a lower alkyl-substituted silyl group, when two of adjacent groups among $R^1$, $R^2$, $R^3$, $R^4$, and $R^5$ are lower alkyl groups, they may combine together to form a 5- or 6-membered ring together with the carbon atoms of the benzene ring to which they bind (this ring may have one or more alkyl groups), and $X^1$ represents —CONH— or —NHCO—.

In the aforementioned general formula (I), as the lower alkyl group represented by $R^1$, $R^2$, $R^3$, $R^4$, and $R^5$, a linear or branched alkyl group having 1 to about 6 carbon atoms, preferably 1 to 4 carbon atoms, can be used. For example, methyl group, ethyl group, n-propyl group, isopropyl group, n-butyl group, sec-butyl group, tert-butyl group, and the like can be used. On the aforementioned lower alkyl group, one or more arbitrary substituents may exist. Examples of the substituents include, for example, hydroxyl group, a lower alkoxyl group, a halogen atom, and the like. Examples of the lower alkyl-substituted silyl group represented by $R^1$, $R^2$, $R^3$, $R^4$, and $R^5$ include, for example, trimethylsilyl group, and the like.

Two of adjacent lower alkyl groups selected from the group consisting of $R^1$, $R^2$, $R^3$, $R^4$, and $R^5$ may combine together to form one or two, preferably one of 5- or 6-membered ring together with the carbon atoms of the benzene ring to which they bind. The ring formed as described above may be saturated or unsaturated, or an aromatic ring, and one or more lower alkyl groups such as methyl group and ethyl group may substitute on the ring. As the alkyl group which may substitute on the ring, a linear or branched alkyl group having 1 to about 6 carbon atoms, preferably 1 to 4 carbon atoms, can be used. For example, methyl group, ethyl group, and the like can be used, and preferably 2 to 4 of methyl groups, more preferably 4 of methyl groups, may substitute. For example, it is preferred that 5,6,7,8-tetrahydronaphthalene ring, 5,5,8,8-tetramethyl-5,6,7,8-tetrahydronaphthalene ring, or the like is formed by the benzene ring on which $R^2$ and $R^3$ substitute, and $R^2$ and $R^3$.

Examples of other preferred retinoids include, for example, retinoids comprising dibenzo[b,f][1,4]thiazepinyl-benzoic acid or dibenzo[b,f][1,4]diazepinylbenzoic acid as the basic skeleton represented by B—X—A. Examples of such retinoids are described in, for example, Japanese Patent Unexamined Publication (KOKAI) No. 10-59951. Particularly preferred examples of such retinoids include, for example, HX630 (4-[2,3-(2,5-dimethyl-2,5-hexano)dibenzo[b,f][1,4]-thiazepin-11-yl]benzoic acid). Further, examples of retinoids wherein X is —N($R^4$)—, and B is an aromatic heterocyclic carboxylic acid include, for example, 2-[2-(N-5,6,7,8-tetrahydro-5,5,8,8-tetramethyl-2-naphthalenyl-N-cyclopropylmethyl)amino]pyrimidine-5-carboxylic acid. The aforementioned HX630 and 2-[2-(N-5,6,7,8-tetrahydro-5,5,8,8-tetramethyl-2-naphthalenyl-N-cyclopropylmethyl) amino]pyrimidine-5-carboxylic acid are retinoids known to be ligands of the receptor RXR. Further, examples of retinoids wherein X is a divalent aromatic group include, for example, 4-[5-(4,7-dimethylbenzofuran-2-yl)pyrrol-2-yl] benzoic acid. Examples of the compound wherein A is a tropolonyl group include, for example, 5-[[5,6,7,8-tetrahydro-5,5,8,8-tetramethyl-2-naphthalenyl]carboxamido] tropolone, and the like.

As the active ingredient of the medicament of the present invention, salts of the aforementioned retinoids may be used. For example, physiologically acceptable salts including metal salts such as sodium salts, potassium salts, magnesium salts, and calcium salts, ammonium salts, organic amine salts such as triethylamine salts, and ethanolamine salts, and the like can be used as the active ingredient of the medicament of the present invention. The aforementioned retinoids may have one or more asymmetric carbons according to the types of substituents, and all of arbitrary optical isomers based on these asymmetric carbons, arbitrary mixtures of optical isomers, racemates, diastereoisomers based on two or more asymmetric carbons, arbitrary mixtures of diastereoisomers, and the like can be used as the active ingredient of the medicament of the present invention. Furthermore, geometrical isomers based on cis- or trans-configuration of double bond, arbitrary mixtures of geometrical isomers, and arbitrary hydrates or solvates of the compounds in free forms or in the form of a salt can also be used as the active ingredient of the medicament of the present invention.

The medicament of the present invention has an action of promoting memory consolidation, and the medicament can be used as, for example, a medicament for prophylactic and/or therapeutic treatment of dysfunction of memory consolidation associated with a neurodegenerative disease, aging, and the like. Examples of the neurodegenerative disease include Alzheimer disease, Parkinson's disease, schizophrenia, drug dependence, abnormality of autonomic nerve, and the like, but not limited to these examples. In the process of memory, short-term memory changes into long-term memory, and consolidated as memory which is not easily forgotten. The medicament of the present invention has an action of improving obstruction of the process of consolidating short-term memory as long-term memory (in the specification, this obstruction is called dysfunction of memory consolidation), and promoting formation of long-term memory from short-term memory. The term long-term memory used in the specification includes declarative memory and procedural memory, and declarative memory includes episodic memory and semantic memory. The medicament of the present invention can improve memory consolidation for any of these types of long-term memory. The memory consolidation promoting action of the medicament of the present invention can be objectively determined by using, for example, a passive avoidance reaction as an index, and the procedures for the determination are specifically described in the examples of the specification. Therefore, those skilled in the art can readily confirm the action of the medicament of the present invention.

The medicament of the present invention contains one or more kinds of substances selected from the group consisting of the aforementioned retinoids, salts thereof, hydrates and solvates thereof as the active ingredient. Preferred efficacy may be obtained by administering two or more kinds of different retinoids in combination. Although the aforementioned substances, per se, may be administered as the medicament of the present invention, they can be preferably administered as a pharmaceutical composition for oral or parenteral administration that can be prepared by methods well known to those skilled in the art. Examples of the pharmaceutical composition suitable for oral administration include, for example, tablets, capsules, powders, subtilized granules, granules, solutions, syrups, and the like, and examples of the pharmaceutical composition suitable for parenteral administration include, for example, injections, suppositories, inhalants, eye drops, nasal drops, ointments, creams, patches, and the like.

The aforementioned pharmaceutical composition can be prepared by adding pharmacologically and pharmaceutically acceptable additives. Examples of the pharmacologically and pharmaceutically acceptable additives include, for example, excipients, disintegrating agents or disintegrating aids, binders, lubricants, coating agents, dyes, diluents, bases, dissolving agents or dissolving aids, isotonic agents, pH modifiers, stabilizers, propellants, tackifiers, and the like.

Dose of the medicament of the present invention is not particularly limited, and can be appropriately increased or decreased depending on various factors which should usually be taken into consideration, such as body weight and age of a patient, symptoms and type of a disease, and administration route. In general, for oral administration, the medicament of the present invention can be used at a dose of about 0.01 to 1,000 mg per day for adults, which may be appropriately increased or decreased.

EXAMPLES

The present invention will be more specifically explained with reference to examples. However, the scope of the present invention is not limited by the following examples.

Example 1

6-Week old Slc:Wistar male rats were used for the experiment after preliminary breeding including one week of quarantine. The animals were individually bred under an environment at a temperature of 22±3° C. and a humidity of 50±20% with illumination of 12 hours (8:00 to 20:00) for both the preliminary breeding and experimental periods, and the animals were given pellets (Labo M R Stock, Nihon Nosan Kogyo K. K.) and tap water ad libitum. The animals were divided into groups according to body weights as an index (10 animals/group), and trials for acquisition and reproduction of memory were performed. Each trial was performed by using a shuttle type avoidance test box. The box had a light room on one side and a darkroom on the other side, an opening-and-closing type partition was provided between the two rooms, and the box was designed so that only the dark room was electrifiable. Each animal was put into the light room, time until the animal moved to the dark room (latent time) was measured up to 5 minutes, and when the rat moved to the darkroom, the partition was shut, and shock was given by electrification.

Each animal was subcutaneously given 0.5 mg/kg of scopolamine 30 minutes before the trial, and this procedure was continued for seven days. Scopolamine, which is an anticholinergic agent, is known to block the muscarinic acetylcholine receptor in the striate body and inhibit acquisition of new memory (Folia Pharmacol. Jpn., 97, pp. 351-359, 1991). From the third day, the test substance (Am80: 4-[(5,6,7,8-tetrahydro-5,5,8,8-tetramethyl-2-naphthalenyl)carbamoyl] benzoic acid, 10 mg/kg/day) was orally given 3 hours before the scopolamine treatment. With numerical values obtained, average and standard deviation were calculated for each group, and a homoscedasticity test was performed by F-test between the control group (no Am80 treatment) and Am80-treated group. When homoscedasticity was observed, presence or absence of significant difference was determined by Student's t-test, and when non-homoscedasticity was observed, presence or absence of significant difference was determined by Aspin-Welch's t-test. The results are shown in Table 1. In the Am80-treated group, the latent time was gradually extended from the start of the treatment, and from the 5th day, significant differences were observed with respect to the control group.

TABLE 1

| Dose | Reaction latency (second) | | | | | | |
|---|---|---|---|---|---|---|---|
| (mg/kg/day) | 1[a] | 2 | 3 | 4 | 5 | 6 | 7 |
| 0 (Control) | 20 ± 4 | 12 ± 4 | 21 ± 5 | 44 ± 10 | 52 ± 6 | 53 ± 4 | 57 ± 7 |
| 10 | 15 ± 4 | 14 ± 4 | 26 ± 5 | 88 ± 19 | 149** ± 29 | 163** ± 30 | 162** ± 29 |

[a]Lapsed days (day)
**p < 0.01, significant difference between the control group and the treatment group as determined by F-t-test
Averages are indicated in the upper row, and standard errors are indicated in the lower row for each group.

Example 2

A test was performed in the same manner as that of Example 1, except that scopolamine was given at a dose of 0.25 mg/kg or 0.5 mg/kg, and 2 mg/kg, 5 mg/kg or 12.5 mg/kg of Am80, 30 mg/kg of Tac101 (4-[(3,5-bis-trimethylsilylphenyl)-carboxamido]benzoic acid), and 10 mg/kg of HX630 (4-[2,3-(2,5-dimethyl-2,5-hexano)dibenzo[b,f][1,4]thiazepin-11-yl]benzoic acid) were given. Combinatory use of Am80 (5 mg/kg) and HX630 (10 mg/kg) was also similarly examined. Drug treatment was performed from the 2nd day. In the same manner as the results of Example 1, the latent time was gradually extended in the Am80, Tac101, HX630-treated groups and the Am80 and HX630 combined use group compared with the control group.

TABLE 2

| Dose (mg/kg/day) | | | | Reaction latency (second) | | | |
|---|---|---|---|---|---|---|---|
| SCP | Am 80 | Tac 101 | HX 630 | 1[a] | 2 | 3 | 4 | 5 |
| 0.5 | — | — | — | 13 ± 2 | 18 ± 3 | 17 ± 2 | 23 ± 3 | 33 ± 1 |
| 0.25 | — | — | — | 10 ± 2 | 15 ± 2 | 15 ± 4 | 30 ± 6 | 42 ± 5 |
| 0.5 | 2 | — | — | 14 ± 5 | 9 ± 1 | 23 ± 3 | 24 ± 3 | 38 ± 3 |
| 0.5 | 5 | — | — | 19 ± 4 | 18 ± 2 | 38 ± 6 | 52 ± 5 | 71 ± 4 |
| 0.5 | 12.5 | — | — | 15 ± 4 | 24 ± 2 | 43 ± 10 | 74 ± 3 | 133 ± 12 |
| 0.25 | 5 | — | — | 14 ± 3 | 15 ± 3 | 53 ± 14 | 80 ± 12 | 155 ± 17 |
| 0.5 | — | 30 | — | 19 ± 9 | 21 ± 4 | 47 ± 7 | 69 ± 3 | 107 ± 4 |
| 0.5 | — | — | 10 | 18 ± 5 | 21 ± 2 | 30 ± 3 | 33 ± 2 | 51 ± 3 |
| 0.5 | 5 | — | 10 | 11 ± 3 | 17 ± 5 | 57 ± 11 | 60 ± 5 | 102 ± 12 |

[a]Lapsed days (day)
Averages are indicated in the upper row, and standard errors are indicated in the lower row for each group.
SCP: Scopolamine

Example 3

In the same manner as that of Example 2, scopolamine was given at a dose of 0.25 mg/kg, and 10 mg/kg of 4-[5-(4,7- dimethylbenzofuran-2-yl)pyrrol-2-yl]benzoic acid (IT-K-1001) was orally given. The results are shown in Table 3. This compound markedly inhibited the effect of scopolamine.

TABLE 3

| Dose (mg/kg/day) | | Reaction latency (second) | | | | | | | |
|---|---|---|---|---|---|---|---|---|---|
| SCP | IT-K-1001 | 1[a] | 2 | 3 | 4 | 5 | 6 | 7 | 8 |
| — | — | 16 ± 4 | 134 ± 50 | 152 ± 41 | 201 ± 24 | 300 ± 0 | 292 ± 8 | 300 ± 0 | 300 ± 0 |
| 0.25 | — | 27 ± 3 | 28 ± 8 | 31 ± 6 | 43 ± 11 | 47 ± 7 | 49 ± 8 | 58 ± 7 | 73 ± 5 |
| 0.25 | 10 | 22 ± 4 | 11 ± 2 | 106 ± 43 | 115 ± 41 | 206 ± 46 | 291 ± 9 | 300 ± 0 | 281 ± 19 |

[a]Lapsed days (day)
Averages are indicated in the upper row, and standard errors are indicated in the lower row for each group.
SCP: Scopolamine

Industrial Applicability

The medicament of the present invention has a superior action for memory consolidation, and is useful as, for example, a medicament for prophylactic and/or therapeutic treatment of dysfunction of memory consolidation associated with neurodegenerative diseases such as Alzheimer disease.

The invention claimed is:

1. A method for promoting formation of long-term memory from short-term memory, comprising administering to a mammal, in need of consolidation of short-term as long-term memory, a therapeutically effective amount of a composition to promote memory consolidation of short-term memory as long-term memory, the composition comprising 4-[(5,6,7,8-tetrahydro-5,5,8,8-tetramethyl-2-naphthalenyl)carbamoyl] benzoic acid as an active ingredient.

2. The method according to claim 1, wherein the promoting formation of long-term memory from short-term memory comprises therapeutic treatment of dysfunction of memory consolidation associated with a neurodegenerative disease.

3. The method according to claim 2, wherein the dysfunction of memory consolidation associated with a neurodegenerative disease comprises Alzheimer disease.

4. The method according to claim 2, wherein the dysfunction of memory consolidation associated with a neurodegenerative disease comprises Parkinson's disease.

5. The method according to claim 2, wherein the mammal is a human.

6. The method according to claim 1, wherein the mammal is a human.

7. The method according to claim 3, wherein the mammal is a human.

* * * * *